United States Patent [19]

Nogawa

[11] Patent Number: 5,004,113

[45] Date of Patent: Apr. 2, 1991

[54] PLUG AND BLOOD CIRCULATION DEVICE WITH THE PLUG

[75] Inventor: Atsuhiko Nogawa, Fuji, Japan

[73] Assignee: Terumo Kabushiki Kaisha, Tokyo, Japan

[21] Appl. No.: 304,593

[22] Filed: Feb. 1, 1989

[30] Foreign Application Priority Data

Feb. 3, 1988 [JP] Japan .................. 63-23354

[51] Int. Cl.$^5$ .............................. B01D 13/00
[52] U.S. Cl. .................. 215/358; 215/361; 604/4; 604/403
[58] Field of Search .................. 604/4–6, 604/321, 326, 403; 128/767, 912; 215/35, 212, 269, 292, 294, 355, 361, 358, 359, 364; 383/96; 222/544–547, 554, 563

[56] References Cited

U.S. PATENT DOCUMENTS

| | | | |
|---|---|---|---|
| 632,575 | 9/1899 | Kilbourn | 215/361 |
| 1,138,764 | 5/1915 | Kline | 215/358 |
| 2,367,883 | 1/1945 | Miller | 215/358 |
| 3,317,071 | 5/1967 | Teeter | 215/361 |
| 3,937,350 | 2/1976 | Jölker | 215/361 |
| 3,991,896 | 11/1976 | Miranda . | |
| 4,268,393 | 5/1981 | Persidsky et al. | 604/6 |
| 4,453,937 | 6/1984 | Kurtz et al. | 604/321 |
| 4,573,980 | 3/1986 | Karrasch et al. . | |
| 4,770,787 | 9/1988 | Heath et al. | 604/4 |

FOREIGN PATENT DOCUMENTS

| | | | |
|---|---|---|---|
| 0069236 | 1/1983 | European Pat. Off. . | |
| 1607872 | 1/1976 | Fed. Rep. of Germany . | |
| 2659811 | 7/1977 | Fed. Rep. of Germany | 215/358 |
| 458157 | 4/1913 | France | 215/361 |
| 1036609 | 12/1950 | France | 215/361 |
| 1036921 | 5/1951 | France | 215/361 |
| 1158152 | 6/1958 | France . | |
| 2227189 | 11/1974 | France . | |
| 1718 | of 1879 | United Kingdom | 215/361 |
| 2002723 | 2/1979 | United Kingdom . | |

Primary Examiner—John D. Yasko
Assistant Examiner—A. Gutowski
Attorney, Agent, or Firm—Burns, Doane, Swecker & Mathis

[57] ABSTRACT

A plug for medical use includes a plug body having a column member made of a soft resilient material, and a core made of a material harder than the soft material of the plug body and disposed in the column member. The core displaces a portion of the column member outwardly and forming an outwardly bulging portion on the column member. The plug is inserted in a female opening of a BCP port of an extracorporeal blood circulation apparatus, for example, to prevent blood from leading from the BCP port.

13 Claims, 7 Drawing Sheets

PLUG AND BLOOD CIRCULATION DEVICE WITH THE PLUG

BACKGROUND OF THE INVENTION

The present invention relates to a plug for closing a hole, an opening, or the like of a container, a tube, or the like to prevent a fluid such as a liquid, for example, from leaking out of the hole, the opening, or the like, and more particularly to a medical plug of such a nature and an instrument equipped with such a plug.

Medical plugs for selectively closing and opening the holes, openings, or the like (hereinafter referred to also as a "hole") of containers, tubes, or the like for medical use, are primarily required to be of such a structure as to hold a fluid against leakage from the holes. These medical plugs are also required to be easily fittable into the holes of container, tubes, or the like for medical use, to be easily removable from the holes after they have been fitted, nevertheless to remain securely retained against accidental removal which would otherwise take place due to shocks, and also to be highly durable during long usage. Conventional medical plugs include:

(1) plugs which can entirely be force-fitted into corresponding holes, the plugs being made of a hard material for greater durability and tapered in the direction in which they can be pulled out;

(2) plugs which can entirely be forced-fitted into corresponding holes, the plugs being made of a soft material for easy removal and higher shock resistance and tapered in the direction (3) plugs which can partly be force-fitted into corresponding holes, such as a sealing member or packing positioned on the front end of the plunger of a syringe and slidably fitted in the cylinder of the syringe.

The medical plug of the group (1), typically a syringe cylinder to be fitted into a hollow needle, is made of a hard material and can be force-fitted into the hole of a medical container, tube, etc. for liquid tightness. While the plug is highly durable, it is not easy to pull the plug out of the hole after it has been fitted in the hole. On the other hand, once the plug is positionally displaced even slightly by a shock applied, the plug tends to become loose in the hole due to the tapered configuration of the plug, with the result that the plug can easily be removed. In order to keep the plug liquid-tight against shocks, the plug has to be force-fitted into the hole more strongly. However, the strongly force-fitted plug cannot be pulled out easily when required. A plug made of a hard material may be designed for being partly force-fitted into a hole, but such a plug would be difficult to manufacture and highly costly.

The medical plug of the class (2), which may be a rubber cap to be fitted in a blood collector tube, is made of a soft material and achieves liquid tightness by being forcibly fitted in its entirety into the hole of a container, tube, or the like. The plug can thus easily be pulled out and is highly resistant to shocks. Since the plug is made of a soft material, however, it is poor in durability and can be deformed during sterilization, particularly autoclave sterilization. Therefore, the plug is normally forced-fitted into the hole under considerably strong forces. As a consequence, the plug cannot easily be fitted into and pulled out of the hole. The plug of the group (2) suffers from the same problem as the plug of the class (1) when it is subjected to shocks.

The medical plug of the kind (3) may typically be a packing to be fitted in the cylinder of a syringe. The plug (packing) of a soft material is partly force-fitted in the hole or space in the cylinder for liquid tightness. While this plug is highly durable, can easily be pulled out, and highly resistant to shocks, it will be fabricated by many manufacturing steps and hence is expensive.

SUMMARY OF THE INVENTION

In view of the aforesaid drawbacks of the conventional plugs, it is an object of the present invention to provide a plug which can easily be fitted into and pulled out of the hole of a container, a tube, or the like for medical use, and which is prevented from accidental removal under shocks, is highly durable, and can easily be manufactured, and also to provide an instrument with such a plug.

Another object of the present invention is to provide a plug comprising: a plug body having a column member made of a soft resilient material; and a core made of a material harder than said soft material of the plug body and disposed in said column member, said core displacing a portion of said column member outwardly and forming an outwardly bulging portion on said column member.

Still another object of the present invention is to provide a plug wherein said bulging portion and said core are substantially complementary in cross-sectional shape perpendicular to the axial direction of said plug body.

Yet another object of the present invention is to provide a plug wherein said column member has an axially extending hole defined therein, said core being fitted in said hole to displace said portion of the column member outwardly and provide said bulging portion.

Yet still another object of the present invention is to provide a plug wherein said hole has an outwardly open end defined in one end of said column member, said core being fitted into said hole through said outwardly open end.

A further object of the present invention is to provide a plug wherein said hole is defined by a tapered surface of said column member which is progressively spread toward said open end.

A still further object of the present invention is to provide a plug wherein said core is larger in size than said open end of said hole, said core being force-fitted into said hole while spreading said open end.

A yet still further object of the present invention is to provide a plug wherein said column member has a partition wall at one end thereof, said partition wall and an outer wall surface of said column member jointly defining therebetween a groove receptive of a projection of a female member into which the plug body can be fitted.

Still another object of the present invention is to provide a plug wherein said column member is cylindrical in shape, said hole being of a circular cross section extending along the axis of said cylindrical column member.

Still another object of the present invention is to provide a plug wherein said core comprises a ball fitted in said hole of a circular cross section.

Yet another object of the present invention is to provide a plug wherein said partition wall comprises an annular wall surrounding said column member.

Yet still another object of the present invention is to provide a plug wherein said annular wall has a tapered wall surface facing said column member.

A further object of the present invention is to provide a plug wherein said plug comprises a medical plug.

It is also an object of the present invention to provide an instrument comprising: a plug comprising a plug body having a column member made of a soft resilient material, and a core disposed in said column member and displacing a portion of said column member outwardly; and an inner wall defining a female opening, said plug being fitted into said female opening to close the female opening and press a portion of said inner wall.

Still another object of the present invention is to provide an instrument wherein said instrument comprises an extracorporeal blood circulation apparatus.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Figure 1:
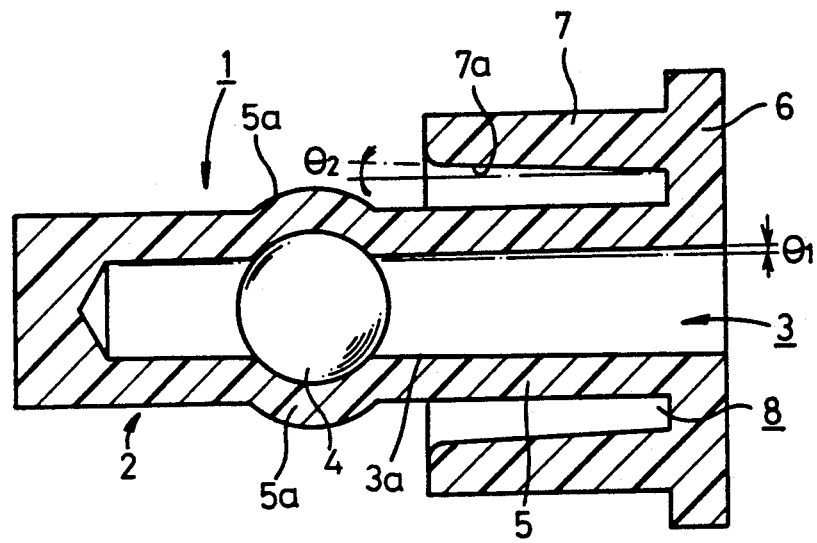
FIG. 1 is a longitudinal cross-sectional view of a plug according to the present invention.

FIG. 1 shows a plug 1 for medical use according to an embodiment of the present invention. The plug 1 is primarily composed of a plug body 2 having a hole (space) 3 defined axially in the plug body 2, and a ball 4 made of a hard material and fitted as a core in the hole 3.

The plug body 2 is made of a soft material such as high polymer elastomer. This soft material is required to have a certain degree of rigidity to make up the plug body 2, and also required to have a certain degree of resiliency since the ball 4, which is larger in diameter than the hole 3 and harder than the plug body 2, is fitted into the hole 3. The soft material of the plug body 2 is further required to withstand a high temperature ranging, for example, from 130° to 140° C. because the plug 1 is subjected to frequent sterilization such as autoclave sterilization as required. The soft material of the plug body 2 needs to be liquid-tight because the plug body 2 will be force-fitted into a BCP (blood cardiotomy plegia) port 30 (FIG. 3) of a blood container 12 to prevent blood B from leaking out of the blood container 12.

Figure 2:
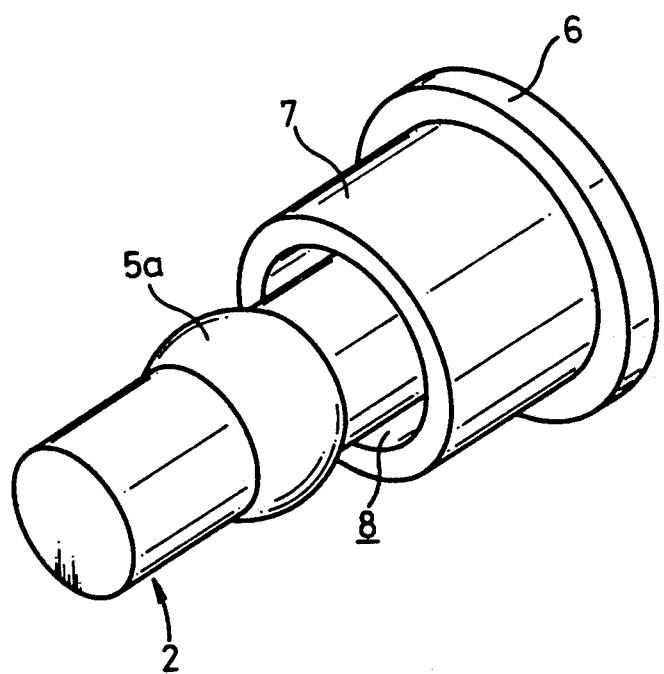
FIG. 2 is a perspective view of the plug shown in FIG. 1.

The plug body 2 has a cylindrical column member 5 with the hole 3 defined therein. The hole 3 is of a circular cross section and extends axially in the cylindrical member 5. The cylindrical member 5 has a flange 6 on an end thereof which is positioned at an open end of the hole 3. The flange 6 has an annular wall 7 larger in diameter than the cylindrical member 5 and having a length which is substantially half the length of the cylindrical member 5, the annular wall 7 being concentric with the cylindrical member 5 (see also FIG. 2). The cylindrical member 5, the flange 6, and the annular wall 7 should preferably be integrally formed as a unitary structure.

The cylindrical member 5 has an inner wall surface defining the hole 3, the inner wall surface being formed as a tapered cylindrical surface $3a$ which is wider in the open inlet end in the flange 6 and becomes progressively narrower toward the inner closed end of the hole 3. The tapered surface $3a$ allows the ball 4 to be inserted easily into the hole 3 and also allows the ball 4 to be force-fitted easily into the hole 3 toward a prescribed position therein. The tapered surface $3a$ is inclined at an angle $\theta_1$, to a broken line lying parallel to the axis of the plug body 2, as shown in FIG. 1.

The annular wall 7 has an inner tapered surface $7a$ which is progressively narrower from the tip end of the annular wall 7 toward the flange 6. The tapered surface $7a$ and the outer circumferential surface of the cylindrical member 5 define an annular groove 8 therebetween for receiving a projection of a female opening in which the plug 1 is to be fitted. The tapered surface $7a$ permits the plug 1 to be force-fitted easily into the BCP port 30 of the blood container 12 since the BCP port 30 has a tapered surface complementary to the tapered surface $7a$. As shown in FIG. 1, the tapered surface $7a$ is inclined at an angle $\theta_2$ to the outer circumferential surface of the cylindrical member 5.

The column member 5 may not necessarily be cylindrical in shape, but may be of another shape such as a prism or the like in complementary relation to the shape of a hole in which the plug body 2 is to be inserted.

The ball 4 is made of stainless steel SUS304 or the like. Instead of the ball, the core may be of a cylindrical shape, a tubular shape, a prismatic shape, or another shape may be fitted in the plug body 2. The core should be of a shape substantially complementary to the cross-sectional shape of the plug body normal to the axis thereof. When the core is fitted in the tube member of the plug body, the core should produce an outwardly bulging portion on the tube member which is substantially complementary in shape to the cross-sectional shape of the tube member. The hole 3 may not necessarily be either left open at one end or defined in the plug body, but the ball 4 may be embedded in the plug body 2 when the plug body 2 is formed.

Figure 6:
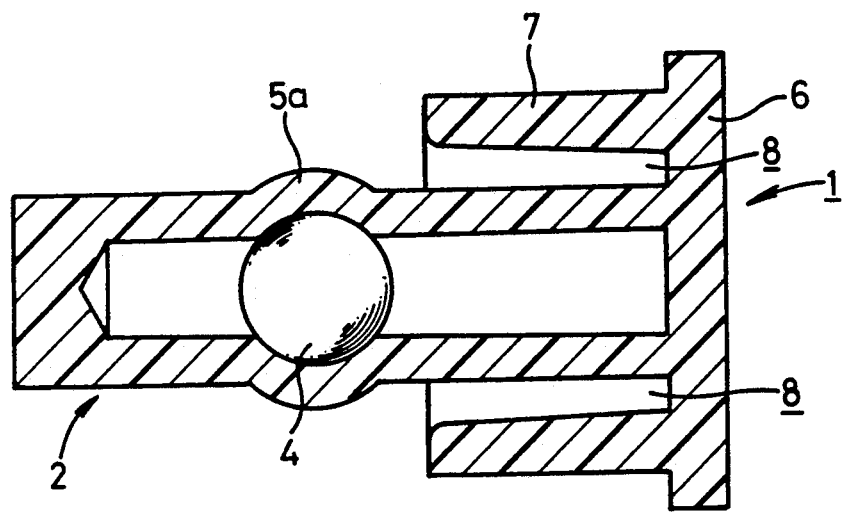
FIG. 6 is a longitudinal cross-sectional view of a plug according to another embodiment of the present invention.
Figure 7:
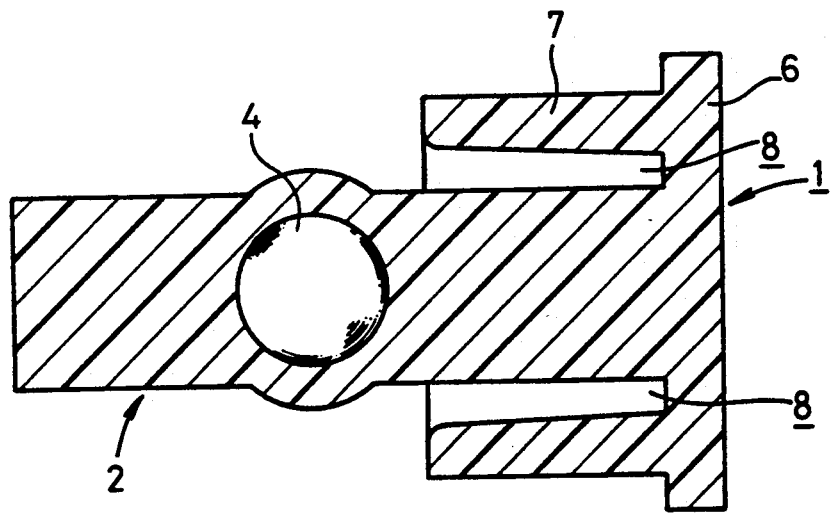
FIG. 7 is a longitudinal cross-sectional view of a plug in accordance with still another embodiment of the present invention.

More specifically, the open end of the the hole 3 in the plug body 2 may be closed by a member integral with the plug body 2, as shown in FIG. 6, or no hole may be defined in the plug body 2 but the ball 4 may be embedded in the plug body 2 which is solid, as shown in FIG. 7.

Figure 3:
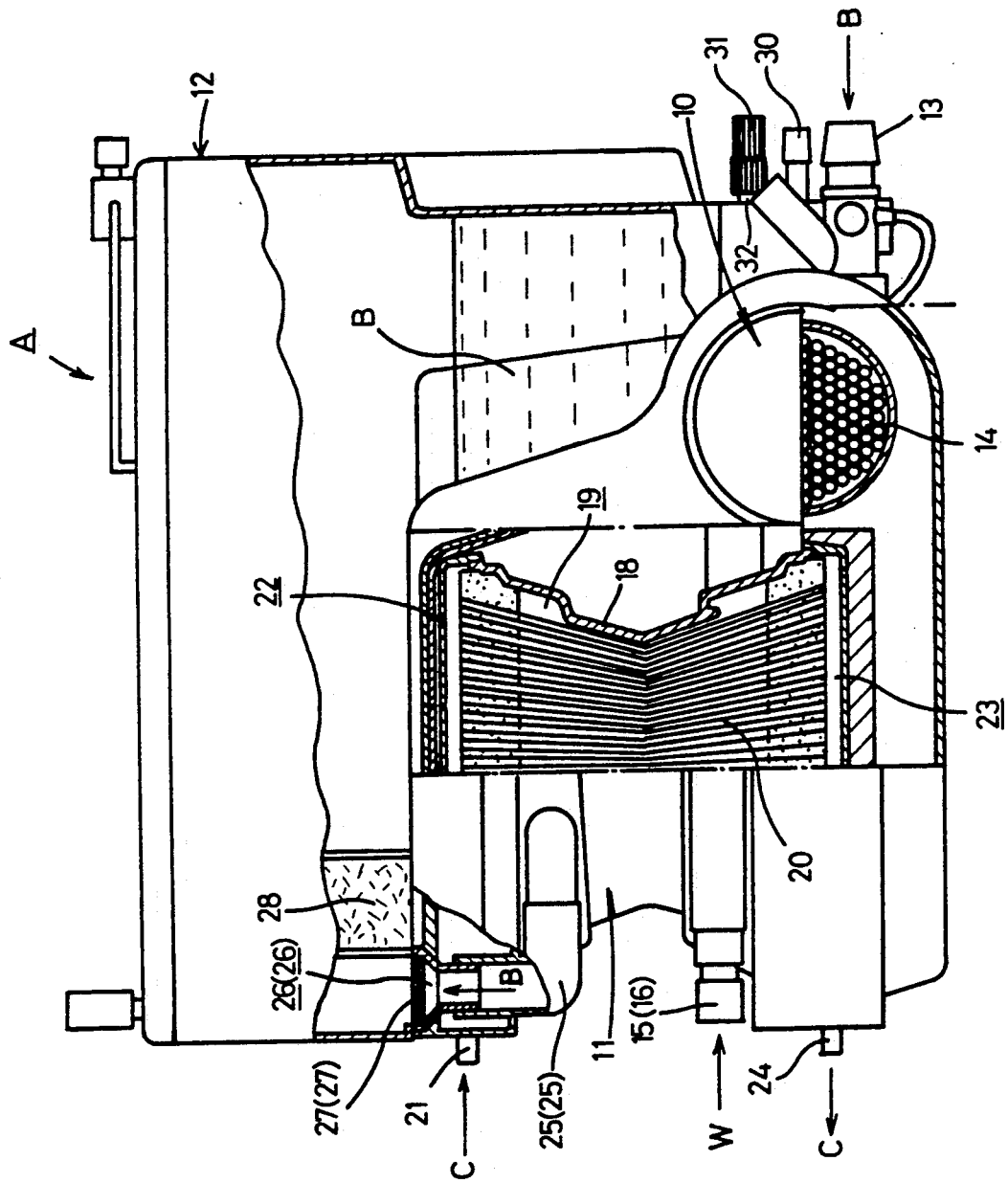
FIG. 3 is a side elevational view, partly in cross section, of an extracorporeal blood circulation apparatus which employs the plug of the invention.
Figure 4:
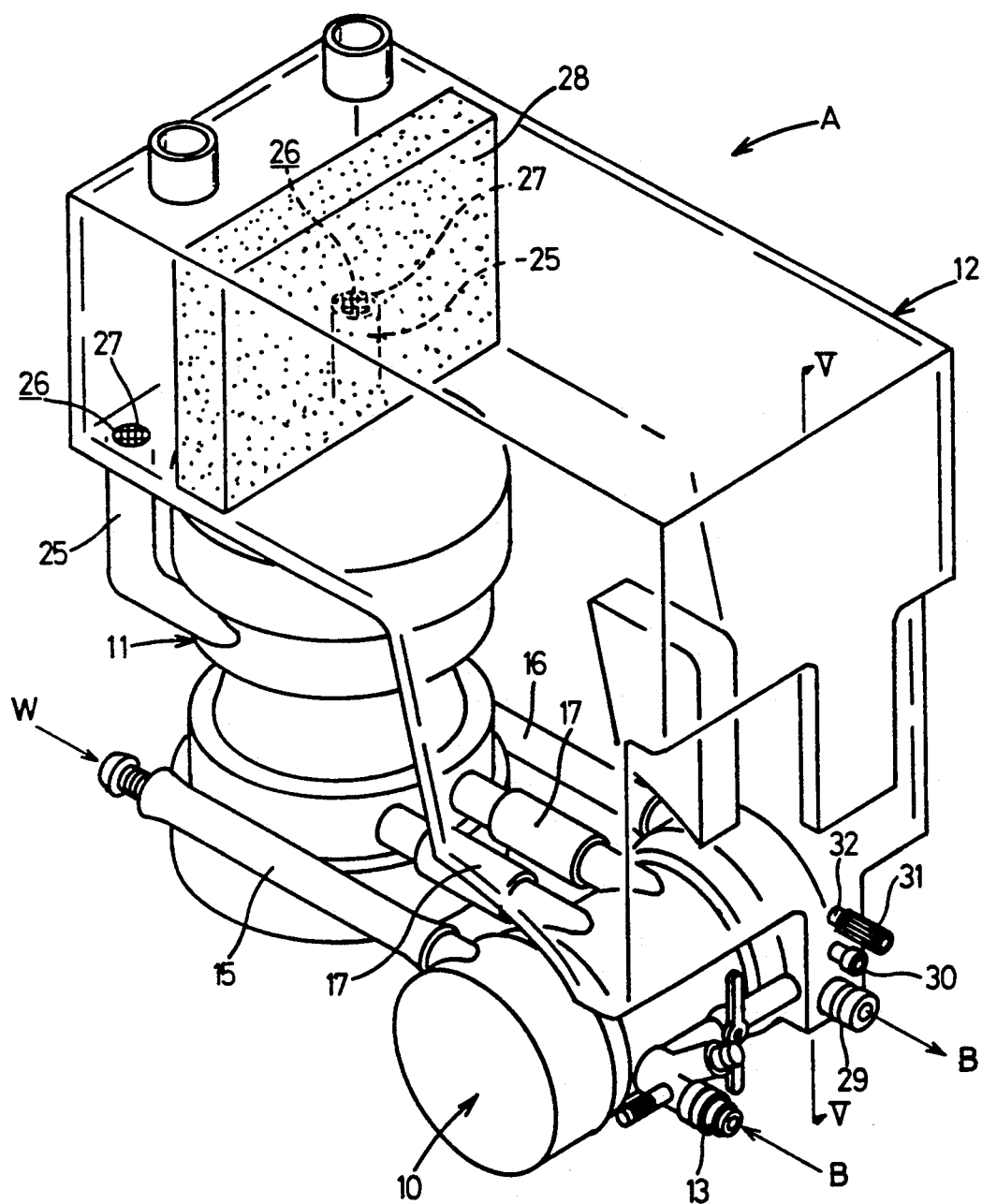
FIG. 4 is a perspective view of the extracorporeal blood circulation apparatus.

The medical plug 1 thus constructed will be used in an extracorporeal blood circulation apparatus (i.e., an instrument with a plug) A, for example, as shown in FIGS. 3 and 4.

The extracorporeal blood circulation apparatus A comprises a heat exchanger 10, an oxygenator 11, and an open-type blood container 12 which are combined as a unit. The basic construction and operation of the extracorporeal blood circulation apparatus A are disclosed in U.S. patent application Ser. No. 196,049, for example.

Blood B flowing from superior and interior vena cavas of a human body through medical tubes (not shown) into a blood supply port 13 is supplied into the oxygenator 11 through gaps between tubes 14 in the heat exchanger 10. The blood B in the heat exchanger 10 is heated or cooled to a predetermined temperature by water W supplied and discharged via water ports 15, 16 and flowing through the tubes 14.

The blood B then flows from the heat exchanger 10 via connector tubes 17 into the oxygenator 11, where oxygen is added to and carbon dioxide is removed from the blood B in a gas exchanger 19 surrounded by a housing 18. More specifically, a gas C containing oxygen is fed from a gas inlet port 21 through a gas supply chamber 22 into a bundle of hollow filamentary membranes 20 housed in the housing 18. An exchange of oxygen and carbon dioxide is carried out in the blood B through the hollow filamentary membranes 20. The gas C which has received carbon dioxide from the blood B is discharged through a gas discharge chamber 23 and a gas outlet port 24 out of the apparatus A.

The blood B which has received oxygen in the oxygenator 11 flows through connector tubes 25 and blood inlet ports 26 into the blood container 12. Before the blood B is stored in the container 12, the flow of the blood B is regulated by mesh screens 27 mounted in the blood inlet ports 26 and any air bubbles are removed from the blood B by a debubblizer 28 of urethane.

A blood outlet port 29, the BCP port 30 (i e., the female opening in which the medical plug 1 can be fitted) for protecting heart muscles, and a port 32 to which a thermistor probe 31 is attached, are mounted on a lower side wall of the blood container 12 near the heat exchanger 10, the ports 29, 30, 32 being successively arranged in the upward direction in the order named. The blood B which is stored in the blood container 12 is fed into an aorta of the human body by a pump (not shown) connected to the blood outlet port 29. The BCP port 30 serves to supply the blood to the coronary artery by blood cardioplegia for protecting the heart muscle during a surgical operation on the heart when the blood of the patient is circulated between the patient and the extracorporeal blood circulation apparatus without passing through the heart while the pulsation of the heart is stopped.

Figure 5:
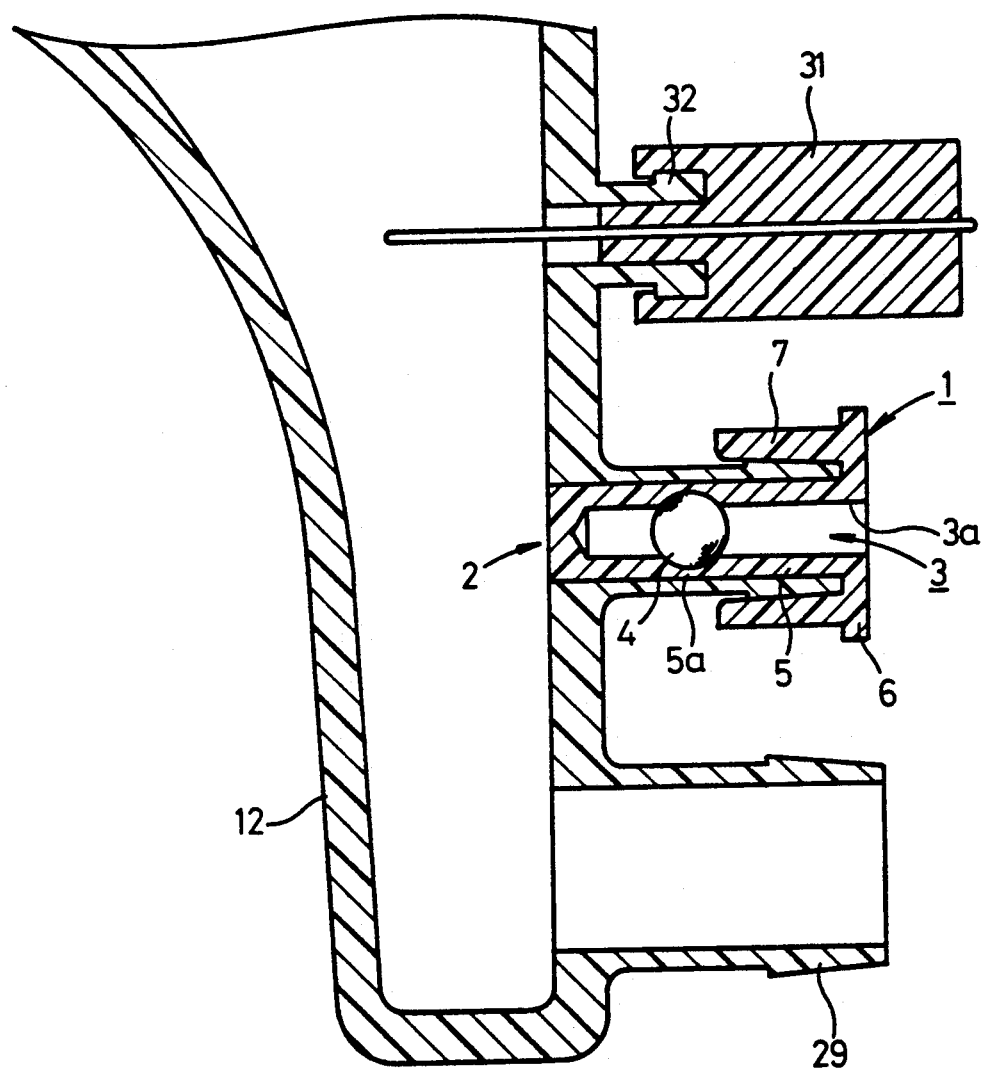
FIG. 5 is an enlarged fragmentary cross-sectional view taken along line V—V of FIG. 4.

If the heart muscles are protected by another method, the BCP port 30 is not used, and the medical plug 1 of the invention is fitted in the BCP port 30 as shown in FIG. 5 to prevent the blood B from leaking out of the BCP port 30. The cylindrical column member 5 of the plug body 2 is inserted in the BCP port 30, or the female opening, of the extracorporeal blood circulation apparatus A. Since the plug body 2 is made of a soft material, a bulging portion 5a of the cylindrical member 5 which is positioned between the ball 4 in the hole 3 and the inner wall surface of the BCP port 30 is collapsed under pressure. The bulging portion 5a is therefore forced-fitted in the inner wall surface of the BCP port 30. Inasmuch as the medical plug 1 is partly force-fitted in the BCP port 30 at the bulging portion 5a, the plug 1 can be pulled out relatively easily by the operator. However, the force-fitted condition of the plug 1, even though partly, is sufficient enough to keep the plug 1 fitted in the BCP port 30 even if shocks are applied, so that no blood will leak out from the BCP port 30 accidentally. The ball 4, which serves as the core in keeping the plug 1 force fitted in the BCP port 30, prevents the plug 1 from being largely deformed by the force-fitted condition and autoclave sterilization, and makes the plug 1 highly durable in use.

Figure 8:
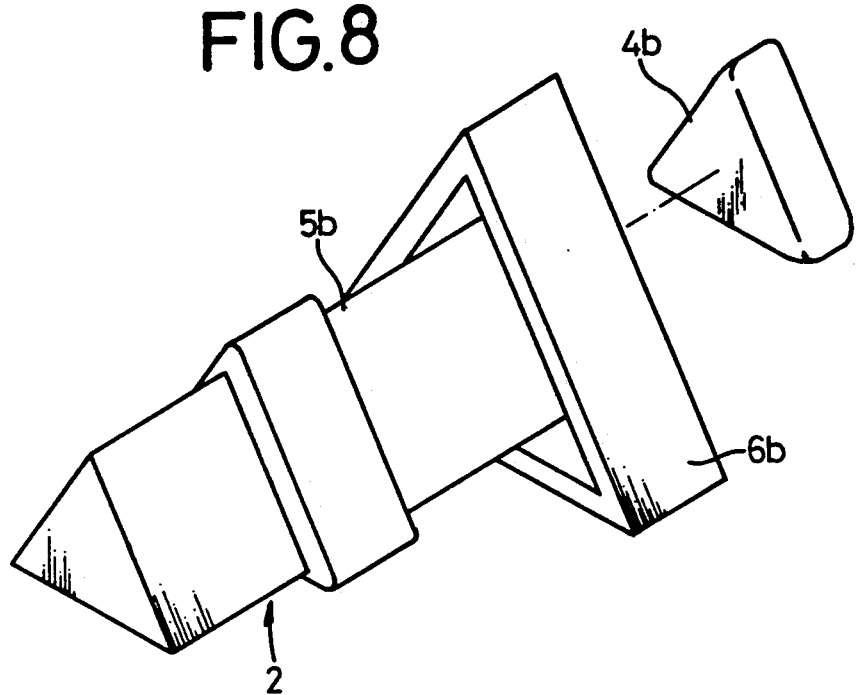
FIG. 8 is a perspective view of a plug according to yet another embodiment of the present invention.
Figure 9:
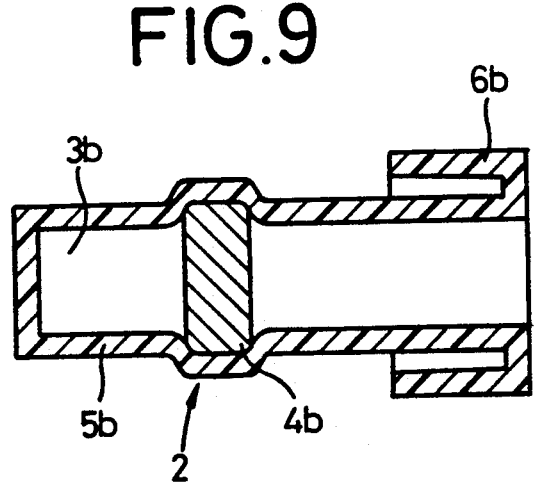
FIG. 9 is a longitudinal cross-sectional view of the plug shown in FIG. 8.

FIGS. 8 and 9 illustrate a plug according to a further embodiment of the present invention. In this embodiment, a plug body 2 has a prismatic member 5b of a triangular cross section having a triangular hole 3b defined therein, and a triangular flange 6b integral with the prismatic member 5b at one end thereof. The plug also includes a triangular core 4b of a hard material which is inserted in the hole 3b to form a bulging portion of a complementary shape on the prismatic member 5b.

Figure 10:
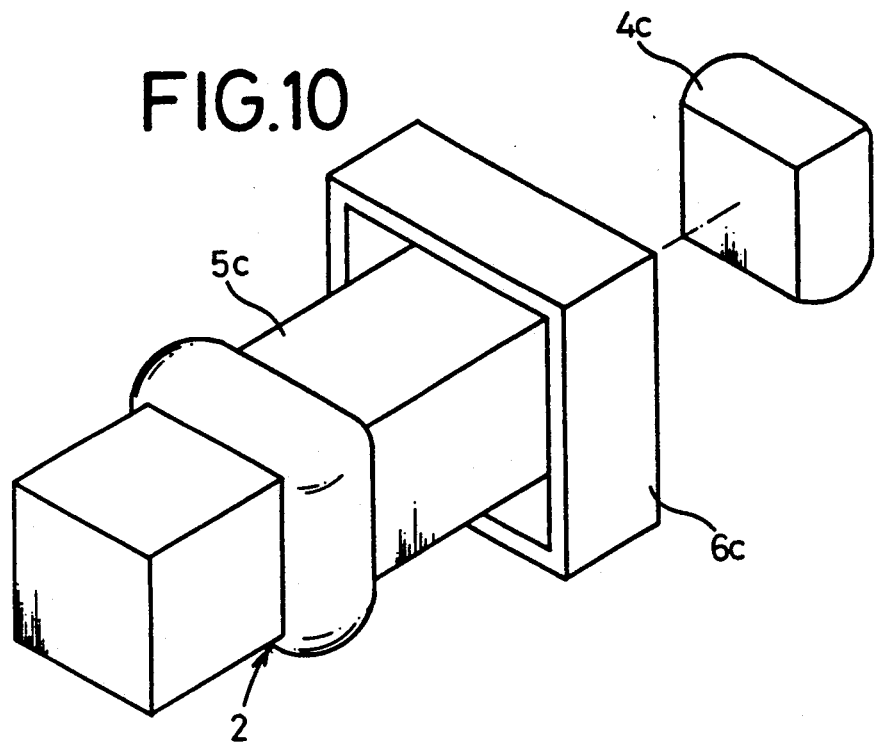
FIG. 10 is a perspective view of a plug according to a further embodiment of the present invention.
Figure 11:
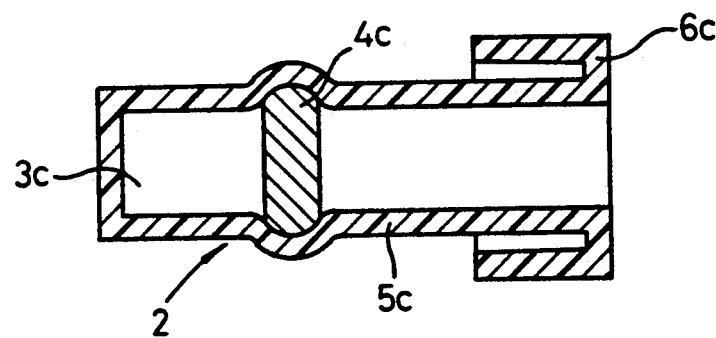
FIG. 11 is a longitudinal cross-sectional view of the plug illustrated in FIG. 10.

FIGS. 10 and 11 show a plug in accordance with a still further embodiment of the present invention. A plug body 2 has a prismatic member 5c of a quadrangular cross section having a quadrangular hole 3c defined therein, and a quadrangular flange 6c integral with the prismatic member 5c at one end thereof The plug further includes a quadrangular core 4c of a hard material which has a vertically elongate elliptical cross-sectional shape. The core 4c is inserted in the hole 3c to form a bulging portion of a complementary shape on the prismatic member 5c.

The plugs shown in FIGS. 8 through 11 has the same advantages as those of the plugs of the preceding embodiments.

With the present invention, as described above, the plug has a column member of a soft resilient material, and a core of a hard material disposed in the column member and forming a bulging portion on the outer circumferential surface of the column member. The instrument with a plug according to the present invention has a female opening with the plug fitted therein. The plug is of a simple structure since it has a plug body of a soft material including the column member with the core of a hard material put in the plug body. By fitting the plug body in the female opening of the instrument which may for example be a container, a tube, or the like for medical use, the core enables the core body to be partly force-fitted at the bulging portion in the female opening. Therefore, the plug body can be pulled out of the opening relatively easily since it is partly fitted in the opening, and can remain fitted in the opening against accidental removal and hence blood leakage due to applied shocks because the plug body is force-fitted in the opening. The core of a hard material in the plug body makes the plug less deformable by the force-fitted condition and autoclave sterilization, and renders the plug highly durable.

Since the plug is simple in structure, it can easily be manufactured and is less costly to manufacture.

Although certain preferred embodiments have been shown and described, it should be understood that many changes and modifications may be made therein without departing from the scope of the appended claims.

What is claimed is:

1. A plug comprising:
   a plug body having a column member made of a soft resilient material;

a core made of a material harder than said soft material of the plug body and disposed in said column member, said core displacing a portion of said column member outwardly and forming an outwardly bulging portion on said column member;

said column member having an axially extending hole defined therein and a flange extending from one end thereof, said hole having an outwardly open end defined in said one end of said column member extending through said flange and a closed end defined in the other end of said column member, said core being fitted in said hole through said outwardly open end to displace said portion of the column member outwardly and provide said bulging portion;

said hole being defined by a tapered surface of said column member which is progressively spread at a constant angle from said closed end through said flange to said open end.

2. A plug comprising:

a plug body having a column member made of a soft resilient material;

a core made of a material harder than said soft material of the plug body and disposed in said column member, said core displacing a portion of said column member outwardly and forming an outwardly bulging portion of said column member;

said column member having a partition wall at one end thereof, said partition wall and an outer wall surface of said column member jointly defining therebetween a groove receptive of a projection of a female member into which the plug body can be fitted;

said partition wall having a length measured parallel to said outer wall surface which is substantially longer than a width of said groove measured perpendicular to said outer wall surface.

3. A plug according to claim 2, wherein said column member has an axially extending hole defined therein, said core being fitted in said hole to displace said portion of the column member outwardly and provide said bulging portion.

4. A plug according to claim 3, wherein said column member is cylindrical in shape, said hole being of a circular cross section extending along the axis of said cylindrical column member.

5. A plug according to claim 4, wherein said core comprises a ball fitted in said hole of a circular cross section.

6. A plug according to claim 4, wherein said partition wall comprises an annular wall surrounding said column member.

7. A plug according to claim 6, wherein said annular wall has a tapered wall surface facing said column member.

8. A plug according to claim 1 or 2, wherein said plug comprises a medical plug.

9. A plug according to claim 1 or 2, wherein said bulging portion and said core are substantially complementary in cross-sectional shape perpendicular to the axial direction of said plug body.

10. A plug according to claim 3, wherein said hole has an outwardly open end defined in one end of said column member, said core being fitted into said hole through said outwardly open end.

11. A plug according to claim 10, wherein said hole is defined by a tapered surface of said column member which is progressively spread toward said open end.

12. A plug according to claim 11, wherein said core is larger in size than said open end of said hole, said core being force-fitted into said hole while spreading said open end.

13. An extracorporeal blood circulation apparatus comprising:

a blood container for storing blood therein;

a plug comprising a plug body having a column member made of a soft resilient material and a core made of a material harder than said soft material of the plug body and disposed in said column member, said core displacing a portion of said column member;

a female opening in said blood container comprising an inner wall, said plug being fitted into said female opening to close the female opening and pressing against a portion of said inner wall, wherein the surface of an end portion of said plug body is substantially flush with an inner wall surface of said blood container;

said column member having a partition wall at one end thereof, said partition wall and an outer wall surface of said column member jointly defining therebetween a groove receptive of a projection of said female opening into which said plug body is fitted.

* * * * *